(12) United States Patent
Pynsent (10) Patent No.: US 8,512,341 B2
(45) Date of Patent: Aug. 20, 2013

(54) MEDICAL DEVICE

(75) Inventor: Tom Pynsent, Alvechurch (GB)

(73) Assignee: Smith & Nephew PLC, London (GB)

( * ) Notice: Subject to any disclaimer, the term of this patent is extended or adjusted under 35 U.S.C. 154(b) by 581 days.

(21) Appl. No.: 12/438,772

(22) PCT Filed: Aug. 30, 2007

(86) PCT No.: PCT/GB2007/003296
§ 371 (c)(1),
(2), (4) Date: Jun. 12, 2009

(87) PCT Pub. No.: WO2008/025993
PCT Pub. Date: Mar. 6, 2008

(65) Prior Publication Data
US 2009/0326536 A1     Dec. 31, 2009

(30) Foreign Application Priority Data

Aug. 31, 2006   (GB) .................................. 0617134.2

(51) Int. Cl.
*A61B 17/00*     (2006.01)
(52) U.S. Cl.
USPC ........................................................ 606/80
(58) Field of Classification Search
USPC ................. 606/79, 80, 84, 85; 408/202, 203, 408/241 S, 227–230
See application file for complete search history.

(56) References Cited

U.S. PATENT DOCUMENTS

| 3,076,356 | A | * | 2/1963 | Simich | 408/223 |
| 3,564,945 | A | * | 2/1971 | Bradley | 408/224 |
| 3,645,640 | A | * | 2/1972 | Zukas | 408/192 |
| 4,560,309 | A | * | 12/1985 | Hornsby | 408/229 |
| 4,993,894 | A | * | 2/1991 | Fischer et al. | 408/14 |
| 5,222,955 | A | | 6/1993 | Mikhail | |
| 5,908,423 | A | * | 6/1999 | Kashuba et al. | 606/80 |
| 5,915,893 | A | * | 6/1999 | Miyanaga | 408/202 |
| 5,957,925 | A | | 9/1999 | Cook et al. | |
| 6,162,226 | A | * | 12/2000 | DeCarlo et al. | 606/80 |
| 6,514,258 | B1 | * | 2/2003 | Brown et al. | 606/80 |
| 7,188,690 | B2 | * | 3/2007 | Geuvers et al. | 175/355 |
| 2004/0267266 | A1 | | 12/2004 | Daniels et al. | |
| 2006/0106393 | A1 | | 5/2006 | Huebner et al. | |

FOREIGN PATENT DOCUMENTS

| CN | 1585623 | 11/2002 |
| DE | 20213728 | 12/2002 |
| EP | 1201191 | 5/2002 |

(Continued)

OTHER PUBLICATIONS

Office Action dated Jun. 9, 2010 in Chinese Application No. 200780040229.6.

(Continued)

*Primary Examiner* — Anu Ramana
(74) *Attorney, Agent, or Firm* — Ropes & Gray LLP (57) ABSTRACT

A cutting tool (1) for cutting bone, comprising: a body (2) having a proximal end (4) and a distal end (6); and at least one primary cutting surface (8) disposed at the distal end (6); wherein the at least one primary cutting surface (8) is shaped so that when, in use, a torque is applied to the proximal end (4) of the body (2), the at least one primary cutting surface (8) cuts a conical or frustoconical shaped cavity in the bone. A method for cutting bone using such a cutting tool (1).

27 Claims, 7 Drawing Sheets

(56) References Cited

FOREIGN PATENT DOCUMENTS

| | | |
|---|---|---|
| GB | 1467332 | 3/1977 |
| GB | 1500360 | 2/1978 |
| GB | 2388321 | 4/2006 |
| WO | WO9624313 | 8/1996 |
| WO | WO 03045257 | 6/2003 |

OTHER PUBLICATIONS

International Search Report dated Jun. 24, 2008 in Application No. PCT/GB2007/003296.

* cited by examiner

MEDICAL DEVICE

CROSS REFERENCE TO RELATED APPLICATIONS

This application is the U.S. national phase of International Application No. PCT/GB2007/003296 filed Aug. 30, 2007 published in English on Mar. 6, 2008 as International Publication No. WO 2008/025993 A2, which application claims priority to Great Britain Application No. 0617134.2 filed Aug. 31, 2006, the contents of each of which are incorporated by reference herein.

This invention relates to medical devices, and in particular cutting tools and alignment devices for cutting bone, especially the femur.

Hip replacements involve the use of an implant stem which is fitted into the medullary canal of the femur. GB 2388321 discloses a particularly effective femoral implant comprising a femoral head at a proximal end thereof, a stem part extending to a distal end of the implant, and a section from which the stem part extends. Said section has an external surface of frustoconical or substantially frustoconical form and it tapers towards said stem part and away from said femoral head. Said femoral head extends directly away from said section to the proximal end of the implant. Said section includes a base portion, at its maximum diameter, which extends substantially axially away from, and is substantially the same diameter as, the end surface of the resected head into which said stem is to be inserted, in use. GB 2388321 also discloses a particularly effective femoral implant stem having the above features without the femoral head. The stem part may be curved or straight.

In the Hip replacement operation using the above femoral implant, the proximal end of the femur is resected and a frustoconical or generally frustoconical shaped cavity is then produced at the upper end of the medullary canal by machining, for example milling. Milling is achieved by using conventional cutting tools such as reamers.

However, producing a frustoconical or generally frustoconical shaped cavity corresponding to the dimensions of the above femoral implants is difficult with conventional cutting tools. The procedure can take several attempts and bone may be damaged. The cavity, particularly the upper end, is often undersized or oversized with respect to the size of the femoral implant. In addition, the cutting tool may be misaligned with the optimal cutting axis. Furthermore, the cutting tool may over-shoot the correct end-point. Consequently, the selected femoral implant does not mate with the cavity properly, leading to instability and/or bone damage.

It is therefore an aim of the present invention to provide a cutting tool and an alignment device that overcomes the above problems.

According to a first aspect of the present invention, there is provided a cutting tool for cutting bone, comprising:
 a body having a proximal end and a distal end; and
 at least one primary cutting surface disposed at the distal end;
 wherein the primary cutting surface is shaped so that when, in use, a torque is applied to the proximal end of the body, the primary cutting surface cuts a conical or frustoconical shaped cavity in the bone.

In this application, a conical or frustoconical shaped cavity includes cavities that are generally (substantially) conical or frustoconical shaped. A frustoconical shaped cavity is a truncated cone shape. The cone or frustum may have straight, substantially straight, curved or substantially curved sides.

The present invention has the advantage that it provides a cutting tool that enables the surgeon to accurately cut a conical or frustoconical shaped cavity in the bone.

The cutting tool may comprise one primary cutting surface disposed at the distal end of the body.

The cutting tool may comprise a plurality of primary cutting surfaces disposed at the distal end of the body. The cutting tool may comprise two to twenty cutting surfaces. The cutting tool may comprise two to ten cutting surfaces. The cutting tool may comprise two, three, four, five, six, or seven cutting surfaces. Preferably, the cutting tool comprises three to six cutting surfaces. More preferably, the cutting tool comprises five cutting surfaces.

The primary cutting surfaces may be disposed equidistantly about the main axis of the body.

The conical section of the primary cutting surfaces may consist of a cone shape. The cone may be formed by a radius of approximately 10-100 mm. Preferably, the cone is formed by a radius of approximately 15-60 mm.

The at least one primary cutting surface may be a cutting tooth. The or each cutting tooth may be fluted. The or each fluted cutting tooth may have a curved cutting edge. The or each fluted cutting tooth may have a linear cutting edge.

The or each cutting tooth may have an average tooth depth of 0.5-10 mm. Preferably, the or each cutting tooth has an average tooth depth of 0.5-4 mm. The or each cutting edge may have a length of 5-200 mm. Preferably, the or each cutting edge has a length of 15-50 mm.

According to embodiments of the present invention, the cutting tool further comprises at least one secondary cutting surface disposed distally to the at least one primary cutting surface, wherein the secondary cutting surface is shaped so that when, in use, a torque is applied to the proximal end of the body, the secondary cutting surface cuts a conical or frustoconical shaped cavity in the bone.

Such embodiments of the invention have the advantage that they enable a surgeon to accurately cut a first conical or frustoconical shaped cavity with the at least one secondary cutting surface and then a second conical or frustoconical shaped cavity with the at least one primary cutting surface in a single procedure using a single tool.

The cutting tool may comprise one secondary cutting surface.

The cutting tool may comprise a plurality of secondary cutting surfaces. The cutting tool may comprise two to twenty cutting surfaces. The cutting tool may comprise two to ten cutting surfaces. The cutting tool may comprise two, three, four, five, six, or seven cutting surfaces. Preferably, the cutting tool comprises three to six cutting surfaces. More preferably, the cutting tool comprises five cutting surfaces.

The secondary cutting surfaces may be disposed equidistantly about the main axis of the body.

The conical section of the secondary cutting surfaces may consist of a cone shape. The cone may be formed by a radius of approximately 10-100 mm. Preferably, the cone is formed by a radius of approximately 15-60 mm.

The at least one secondary cutting surface may be a cutting tooth. The or each cutting tooth may be fluted. The or each fluted cutting tooth may have a curved cutting edge. The or each fluted cutting tooth may have a linear cutting edge.

The or each cutting tooth may have an average tooth depth of 0.5-10 mm. Preferably, the or each cutting tooth has an average tooth depth of 0.5-4 mm. The or each cutting edge may have a length of 5-200 mm. Preferably, the or each cutting edge has a length of 15-50 mm.

The following features apply to embodiments according to the first aspect or the second aspect of the invention.

The proximal end of the body may have a means for releasably connecting to a rotary power source. The rotary power source may be a drill.

The total length of the cutting tool may be in the range 15-400 mm. The total length may be in the range 120-250 mm. Preferably, the total length is in the range 150-170 mm.

The body of the cutting tool may be a shaft. The shaft may be cylindrical. The shaft may be oblong.

The cutting tool may be cannulated. A conduit may extend through the body of the cutting tool. The conduit may extend through the or each primary cutting surface. The conduit may extend through the or each secondary cutting surface. The conduit may be shaped so as to receive a guide rod, in use.

The or each primary cutting surface may be disposed off axis with respect to the conduit axis so that they do not interfere with the guide rod that is received by the conduit. The or each secondary cutting surface may be disposed off axis with respect to the conduit axis so that they do not interfere with the guide rod that is received by the conduit.

The conduit may have a diameter in the range 2-20 mm. The conduit may have a diameter in the range 4-10 mm. Preferably, the conduit has a diameter in the range 5-6 mm.

The cutting tool may comprise a means for attaching to an alignment device.

The cutting tool may be made of a single material. The cutting tool may be made of two or more materials. The cutting tool may be made of a plastic material. The cutting tool may be made of metal. The metal may be titanium. The metal may be stainless steel. The cutting tool may be made of an alloy.

The bone may be a femur. The femur may be resected.

According to a second aspect of the present invention, there is provided a device for aligning a cutting tool with a bone, comprising:

a body having an internal surface and an external surface, the internal surface being shaped so as to accommodate, in use, a cutting tool and the end of a bone, the body having a proximal end and a distal end, the proximal end having an attachment means for releasably attaching, in use, the cutting tool, wherein, in use, the cutting tool is releasably attached to the attachment means and the body engages the end of the bone such that the cutting tool is aligned with the bone and the cutting depth of the cutting tool is limited.

The alignment device of the present invention has the advantage that it aligns the cutting tool with the optimal cutting axis and it prevents the cutting tool from over-shooting the correct end-point.

The body may be a cylinder, the distal end of the cylinder being open and the proximal end being partially closed such that it can engage, in use, the end of the bone.

The cylinder may have continuous sides.

The cylinder may have castellated sides.

The body may have a diameter in the range 10-100 mm. The body may have a diameter in the range 20-70 mm. The body may have a length in the range 10-200 mm. The body may have a length in the range 20-40 mm.

The internal surface may have at least one projection disposed perpendicular or substantially perpendicular to the majority of the internal surface, wherein, in use, the at least one projection engages with the end of the bone, thereby limiting the cutting depth of the cutting tool.

The at least one projection may be disposed near to the proximal end of the body. The at least one projection may be disposed near to the distal end of the body. The at least one projection may be disposed near to the mid-point between the proximal and distal ends of the body.

The at least one projection may be a single post or the like. The at least one projection may be a plurality of posts or the like.

The at least one projection may be a ledge. The ledge may be continuous, extending around the internal surface.

The at least one projection may be a plurality of ledges spaced around the internal surface.

The attachment means may comprise a bayonet fitting which engages, in use, with at least one corresponding lug on the cutting tool.

The attachment means may comprise at least one spring-loaded ball bearing that releasably engages, in use, with a corresponding recess in the cutting tool.

The alignment device may be made of a single material. The alignment device may be made of two or more materials. The alignment device may be made of a plastic material. The alignment device may be made of metal. The metal may be titanium. The metal may be stainless steel. The alignment device may be made of an alloy.

The bone may be a femur. The femur may be resected.

According to a third aspect of the present invention, there is provided an apparatus for cutting bone, comprising a cutting tool according to the first aspect of the present invention in combination with a device according to the second aspect of the present invention.

The device may be releasably attached to the cutting tool. The device may be fixedly attached to the cutting tool.

The apparatus may be made of a single material. The apparatus may be made of two or more materials. The apparatus may be made of a plastic material. The apparatus may be made of metal. The metal may be titanium. The metal may be stainless steel. The apparatus may be made of an alloy.

According to a fourth aspect of the present invention, there is provided a system for cutting bone, comprising:

at least one cutting tool according to the first aspect of the present invention; and at least one device according to the second aspect of the present invention.

The system may comprise a plurality of cutting tools. The cutting tools may differ in the number of primary and/or secondary cutting surfaces. The cutting tools may differ in the shape of the primary and/or secondary cutting surfaces. The system may comprise a plurality of devices.

A surgeon can select appropriate cutting tools and alignment devices according to the various embodiments of the invention as hereinbefore described depending on his/her particular requirements.

According to a fifth aspect of the present invention, there is provided a method for cutting bone, comprising:

preparing a resected bone;

providing a cutting tool, the cutting tool comprising a body having a proximal end and a distal end, and at least one primary cutting surface disposed at the distal end, wherein the at least one primary cutting surface is shaped so that when, in use, a torque is applied to the proximal end of the body, the at least one primary cutting surface cuts a conical or frustoconical shaped cavity in the bone; and applying a torque to the proximal end of the body so that the at least one primary cutting surface cuts a conical or frustoconical shaped cavity in the bone.

According to embodiments of the present invention, the method of the fifth aspect of the present invention may further comprise:

providing a second cutting tool, the second cutting tool comprising a body having a proximal end and a distal end, and at least one primary cutting surface disposed at the distal end, wherein the at least one primary cutting surface is shaped so that when, in use, a torque is applied to the proximal end of the body, the at least one primary cutting surface cuts a conical or frustoconical shaped cavity in the bone, the second cutting tool further comprising at least one secondary cutting surface disposed distally to the at least one primary cutting surface, wherein the at least one secondary cutting surface is shaped so that when, in use, a torque is applied to the proximal end of the body, the at least one secondary cutting surface cuts a conical or frustoconical shaped cavity in the bone; and applying a torque to the proximal end of the body of the second cutting tool so that the at least one secondary cutting surface cuts a conical or frustoconical shaped cavity in the bone.

Thus, the surgeon can prepare a first conical or frustoconical shaped cavity in the bone using the cutting tool of the fifth aspect. The surgeon may then use a second cutting tool to prepare a second conical or frustoconical shaped cavity distal to the first cavity. The surgeon may continue cutting with the second cutting tool so that the at least one primary cutting surface cuts a conical or frustoconical shaped cavity in the bone.

According to a sixth aspect of the present invention, there is provided a method for cutting bone, comprising:

preparing a resected bone;

providing a cutting tool, the cutting tool comprising a body having a proximal end and a distal end, and at least one primary cutting surface disposed at the distal end, wherein the at least one primary cutting surface is shaped so that when, in use, a torque is applied to the proximal end of the body, the at least one primary cutting surface cuts a conical or frustoconical shaped cavity in the bone, the cutting tool further comprising at least one secondary cutting surface disposed distally to the at least one primary cutting surface, wherein the at least one secondary cutting surface is shaped so that when, in use, a torque is applied to the proximal end of the body, the at least one secondary cutting surface cuts a conical or frustoconical shaped cavity in the bone; and applying a torque to the proximal end of the body so that the at least one secondary cutting surface cuts a conical or frustoconical shaped cavity in the bone before the at least one primary cutting surface cuts a conical or frustoconical shaped cavity in the bone.

Thus, the surgeon can accurately cut a first conical or frustoconical shaped cavity with the at least one secondary cutting surface and then a second conical or frustoconical shaped cavity with the at least one primary cutting surface in a single procedure using a single tool.

According to embodiments of the present invention, the methods of the fifth or sixth aspects of the present invention may further comprise:

inserting a guide bar in the resected bone;

providing a cutting tool according to the first aspect of the present invention that is cannulated;

passing the cutting tool down over the guide bar; and cutting the bone.

Thus, the surgeon can use cannulated cutting tools according to the first aspect of the present invention. This has the advantage that the alignment of the cutting tool is optimised.

According to embodiments of the present invention, the methods of the fifth or sixth aspects of the present invention may further comprise:

providing a cutting tool according to the first aspect of the present invention comprising a means for attaching to an alignment device.

providing an alignment device according to the second aspect of the present invention;

attaching the alignment device to the cutting tool; and cutting the bone.

Thus, the surgeon can use a cutting tool according to the first aspect of the present invention with an alignment device according to the second aspect of the present invention. This has the advantage that the alignment of the cutting tool is optimised and over-shooting is prevented. The surgeon may also use a guide bar as described above to optimise alignment.

The methods of the fifth or sixth aspects of the present invention may include cutting tools having any of the features of the first aspect of the present invention as hereinbefore described. The methods of the fifth or sixth aspects of the present invention may include alignment devices having any of the features of the second aspect of the present invention as hereinbefore described.

According to a seventh aspect of the present invention, there is provided a method for cutting bone, comprising:

preparing a resected bone;

providing an apparatus, the apparatus comprising a cutting tool according to the first aspect of the present invention in combination with a device according to the second aspect of the present invention; and applying a torque to the proximal end of the body so that the at least one primary and/or the at least one secondary cutting surface cuts a conical or frustoconical shaped cavity in the bone.

In the methods of the fifth, sixth or seventh aspects of the present invention, the bone may be a femur.

Reference will now be made, by way of example, to the accompanying drawings, in which.

Figure 1:
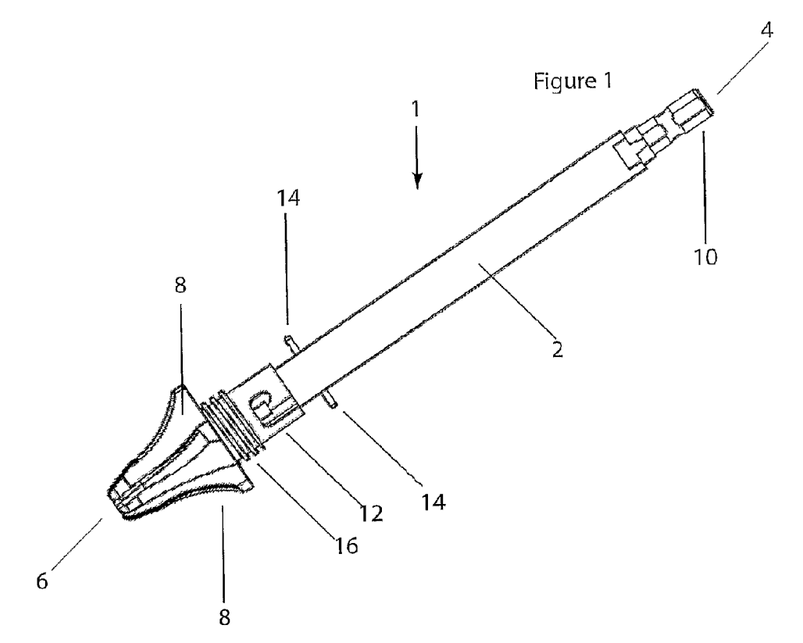
FIG. 1 shows a side view of a cutting tool according to an embodiment of the present invention.

FIG. 1 shows a side view of a cutting tool (1) according to an embodiment of the present invention. The cutting tool comprises a body (2) in the form of a shaft (2) having a proximal end (4) and a distal end (6). Five (only three are shown) primary cutting surfaces (8) in the form of fluted teeth are disposed at the distal end (6) of the shaft (2). The cutting surfaces are disposed equidistantly about the main axis of the shaft (2). The primary cutting surfaces are shaped so that when a torque is applied to the proximal end (4) of the shaft (2), the primary cutting surfaces cut a frustoconical or substantially frustoconical shaped cavity in the bone.

The conical section of the primary cutting surfaces (8) consists of a cone shape. The cone is formed by a radius of approximately 15 to 60 mm. The proximal end diameter of the cone can range between approximately 15-60 mm. Preferably, the diameter ranges between approximately 25-45 mm.

The five fluted teeth (8) extend the full length of the cone with an average tooth depth of approximately 1.5-3.5 mm, preferably around 3 mm. The tooth form flows out of the proximal end of the cone to allow debris to escape.

In an alternative embodiment of the invention (not shown), the primary cutting surfaces are shaped so that when a torque is applied to the proximal end (4) of the shaft (2), the primary cutting surfaces cut a conical or substantially conical shaped cavity in the bone.

The proximal end (4) of the shaft (2) has a means (10) for reversibly connecting to a power source (not shown). The connection means (10) may be a standard drive connection for releasable connection to a power drill source or the like.

The cutting tool (1) has a means (12) for releasably attaching an alignment device (52), such as that shown in FIGS. 4 to 10. The attachment means (12) comprises two male lugs (14) attached to the shaft (2) proximal to the cutting surfaces (8). The male lugs (14) engage with corresponding L-shaped grooves (74) in the alignment device (52) (see FIGS. 7 and 8). The attachment means also comprises a spring (16) attached to the shaft proximal and adjacent to the cutting surfaces (8). When the alignment device (52) is attached to the cutting tool (1) the spring is put under load and the tension of the spring releasably locks the alignment device (52) in position.

In an alternative embodiment of the invention (not shown), the attachment means comprises corresponding threads located on the shaft of the cutting tool (proximal to the cutting surfaces) and the alignment device.

The shaft (2) has a length of approximately 80-200 mm measured between the proximal end of the attachment means (12) and the distal end of the connection means (10). The shaft (2) diameter may be approximately 5-15 mm along this length.

The whole length of the cutting tool (1) can be cannulated in order to accommodate a guide rod, in use. The average cannulation diameter may be 4-10 mm, preferably 5-6 mm.

Figure 2:
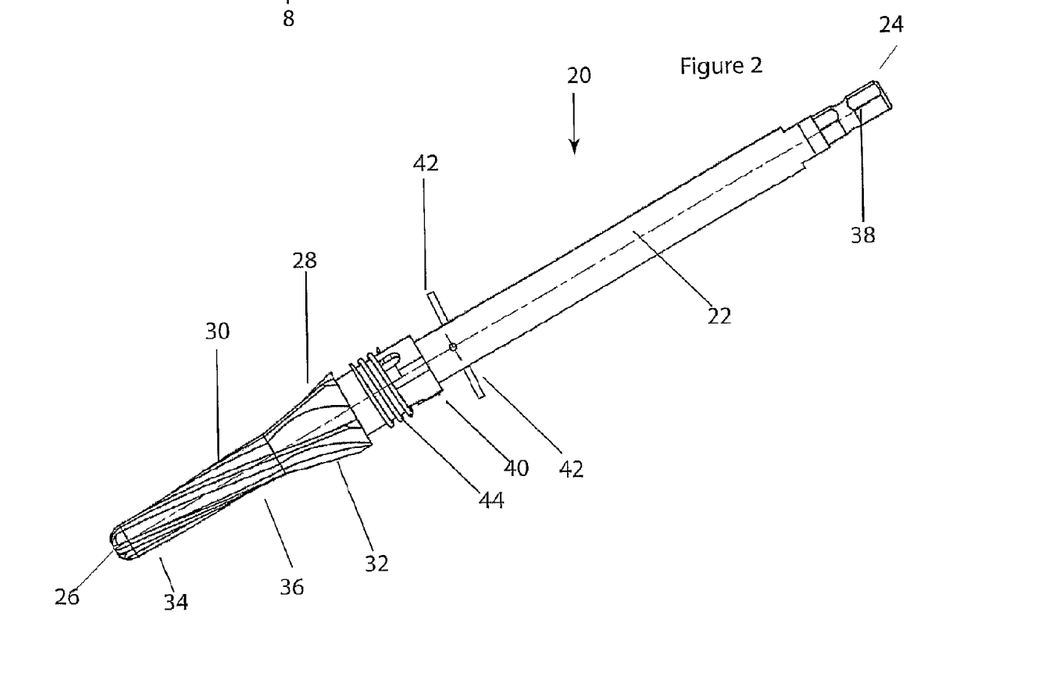
FIG. 2 shows a side view of a cutting tool according to an embodiment of the present invention.

FIG. 2 shows aside view of a cutting tool (20) according to another embodiment of the present invention. The cutting tool (20) comprises a body (22) in the form of a shaft (22) having a proximal end (24) and a distal end (26). Five (only two are shown) primary cutting surfaces (28) in the form of angled teeth are disposed at the distal end (26) of the shaft (22). The primary cutting surfaces (28) are disposed equidistantly about the main axis of the shaft (22). The cutting tool also comprises five (only two are shown) secondary cutting surfaces (30) in the form of angled teeth disposed distally to the primary cutting surfaces (28). The secondary cutting surfaces (30) are disposed equidistantly about the main axis of the shaft (22).

The primary cutting surfaces (28) and the secondary cutting surfaces (30) together form the first (32) and second (34) parts, respectively, of a tapered portion (36). The first part (32) of the tapered portion (36) may have an inclusive angle of approximately 10 to 35 degrees depending on the size of the cutting tool (20). The taper length of the first part (32) may be approximately 5 to 40 mm, preferably 5 to 20 mm, depending on the size of the cutting tool (20). The second part (34) of the tapered portion (36) may have an inclusive angle of approximately 2 to 10 degrees, preferably 3 to 5 degrees depending on the size of the cutting tool (20). The taper length of the second part (32) may be approximately 30 to 100 mm, preferably 50 to 70 mm, depending on the size of the cutting tool (20). The average tooth depth along the length of the tapered portion (36) may be approximately 1.5-3.5 mm, preferably 3 mm. The tooth form of the cutting surfaces (28,30) flows out of the proximal end of the tapered portion (36) enabling debris to escape.

The primary (28) and secondary (30) cutting surfaces are shaped so that when a torque is applied to the proximal end (24) of the shaft (22), the primary (28) and secondary (30) cutting surfaces cut a frustoconical or substantially frustoconical shaped cavity in the bone.

In an alternative embodiment of the invention (not shown), the secondary cutting surfaces are shaped so that when a torque is applied to the proximal end (4) of the shaft (2), the secondary cutting surfaces cut a conical or substantially conical shaped cavity in the bone.

The proximal end (24) of the shaft (22) has a means (38) for reversibly connecting to a power source (not shown). The connection means (38) may be a standard drive connection for releasable connection to a power drill source or the like.

The cutting tool (20) has a means (40) for releasably attaching an alignment device (52), such as that shown in FIGS. 4 to 8. The attachment means (40) comprises two male lugs (42) attached to the shaft (22) proximal to the primary cutting surfaces (28). The male lugs (42) engage with corresponding L-shaped grooves (74) in the alignment device (52). The attachment means (40) also comprises a spring (44) attached to the shaft (22) proximal and adjacent to the cutting surfaces (28). When the alignment device (52) is attached to the cutting tool (20) the spring (44) is put under load and the tension of the spring releasably locks the alignment device (52) in position.

In an alternative embodiment of the invention (not shown), the attachment means comprises corresponding threads located on the shaft of the cutting tool (proximal to the cutting surfaces) and the alignment device.

The shaft (22) has a length of approximately 80-200 mm measured between the proximal end of the attachment means (40) and the distal end of the connection means (38). The shaft (22) diameter may be approximately 5-15 mm along this length.

The whole length of the cutting tool (20) can be cannulated in order to accommodate a guide rod, in use. The average cannulation diameter may be 4 to 10 mm, preferably 5 to 6 mm.

Figure 3:
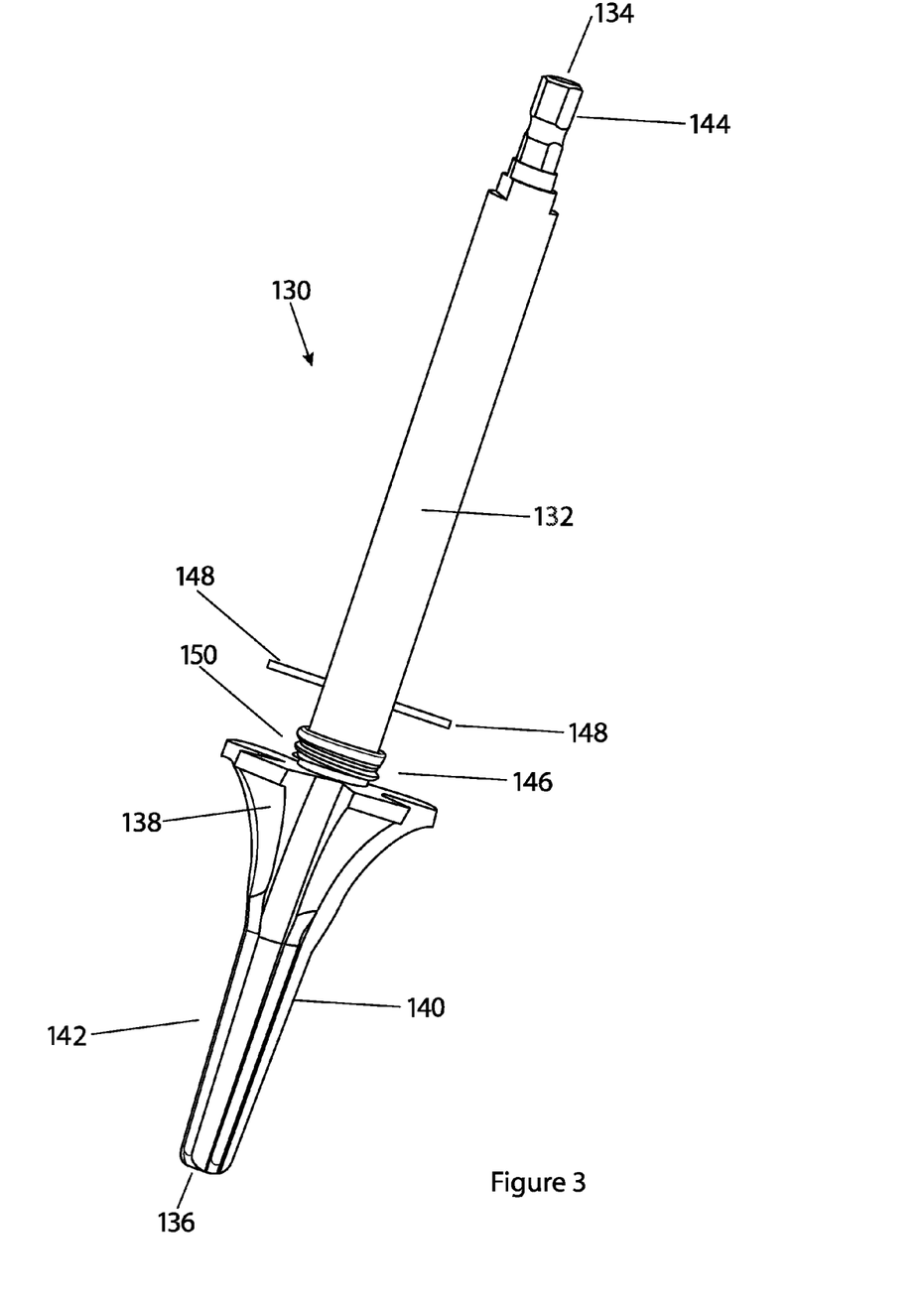
FIG. 3 shows a side view of a cutting tool according to an embodiment of the present invention.

FIG. 3 shows a side view of a cutting tool (130) according to another embodiment of the present invention. The cutting tool (130) combines some of the features of the cutting tools (1, 20) of FIGS. 1 and 2.

The cutting tool (130) comprises a body (132) in the form of a shaft (132) having a proximal end (134) and a distal end (136). Five (only three are shown) primary cutting surfaces (138) in the form of fluted teeth are disposed at the distal end (136) of the shaft (132). The cutting surfaces are disposed equidistantly about the main axis of the shaft (132). The primary cutting surfaces are shaped so that when a torque is applied to the proximal end (134) of the shaft (132), the primary cutting surfaces cut a frustoconical or substantially frustoconical shaped cavity in the bone. The cutting tool also comprises five (only three are shown) secondary cutting surfaces (140) in the form of angled teeth disposed distally to the primary cutting surfaces (138). The secondary cutting surfaces (140) are disposed equidistantly about the main axis of the shaft (132).

The conical section of the primary cutting surfaces (138) consists of a cone shape. The cone is formed by a radius of approximately 15 to 60 mm. The proximal end diameter of the cone can range between approximately 15-60 mm. Preferably, the diameter ranges between approximately 25-45 mm. The distal end of the cone tapers inwards to a diameter of approximately 10 to 15 mm, preferably approximately 8 to 13 mm. At this point the secondary cutting surfaces (140) extend distally.

The five fluted teeth (138) extend the full length of the cone with an average tooth depth of approximately 1.5-3.5 mm, preferably 3 mm. The tooth form flows out of the proximal end of the cone to allow debris to escape.

The secondary cutting surfaces (140) form a tapered portion (142) which may have an inclusive angle of approximately 2 to 10 degrees, preferably approximately 3 to 5 degrees, depending on the size of the cutting tool (130). The taper length of the tapered portion (142) may be approximately 30 to 100 mm, preferably approximately 50 to 70 mm, depending on the size of the cutting tool (130). The tooth form of the cutting surfaces (140) flows out of the proximal end of the tapered portion (142) enabling debris to escape.

The primary (138) and secondary (140) cutting surfaces are shaped so that when a torque is applied to the proximal end (134) of the shaft (132), the primary (138) and secondary (140) cutting surfaces cut a frustoconical or substantially frustoconical shaped cavity in the bone.

In an alternative embodiment of the invention (not shown), the secondary cutting surfaces are shaped so that when a torque is applied to the proximal end (134) of the shaft (132), the secondary cutting surfaces cut a conical or substantially conical shaped cavity in the bone.

The proximal end (134) of the shaft (132) has a means (144) for reversibly connecting to a power source (not shown). The connection means (144) may be a standard drive connection for releasable connection to a power drill source or the like.

The cutting tool (130) has a means (146) for releasably attaching an alignment device (52), such as that shown in FIGS. 4 to 8. The attachment means (146) comprises two male lugs (148) attached to the shaft (132) proximal to the primary cutting surfaces (138). The male lugs (148) engage with corresponding L-shaped grooves (74) in the alignment device (52). The attachment means (146) also comprises a spring (150) attached to the shaft (132) proximal and adjacent to the cutting surfaces (138). When the alignment device (52) is attached to the cutting tool (130) the spring (50) is put under load and the tension of the spring releasably locks the alignment device (52) in position.

In an alternative embodiment of the invention (not shown), the attachment means comprises corresponding threads located on the shaft of the cutting tool (proximal to the cutting surfaces) and the alignment device.

The shaft (132) has a minimum length of approximately 80-200 mm measured between the proximal end of the attachment means (146) and the distal end of the connection means (144). The shaft (132) diameter may be approximately 5-15 mm along this length.

The whole length of the cutting tool (130) can be cannulated in order to accommodate a guide rod, in use. The average cannulation diameter may be approximately 4-10 mm, preferably 5-6 mm.

Figure 4:
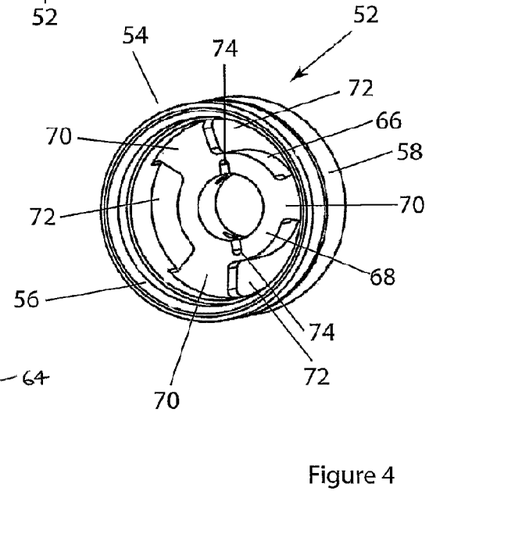
FIG. 4 shows a perspective view of an alignment device according to an embodiment of the present invention.
Figures 5, 8:
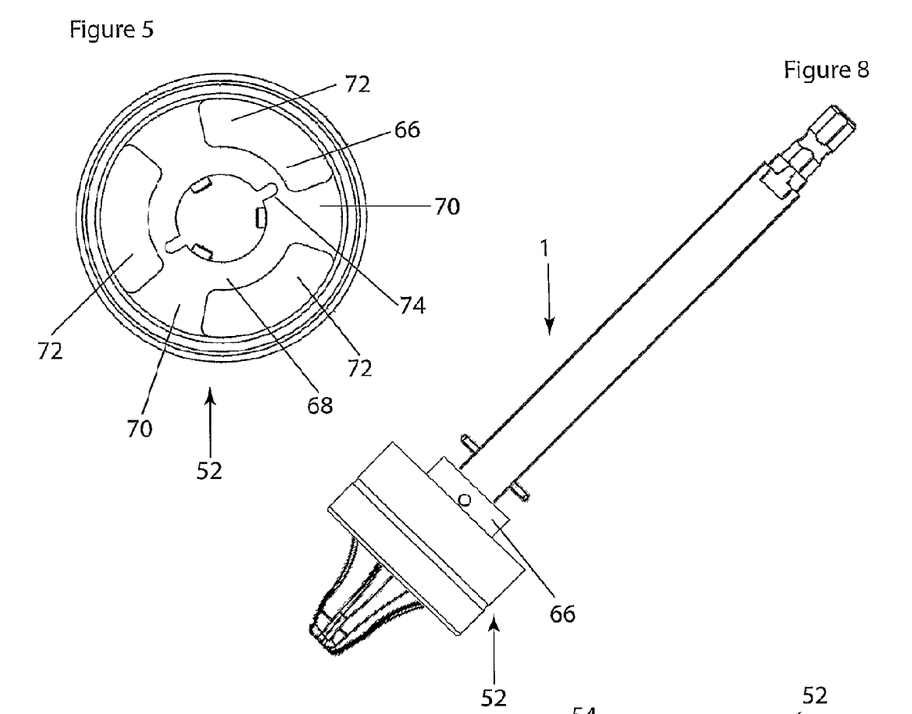
FIG. 5 shows a top plan view of the alignment device of FIG. 4.
FIG. 8 shows a side view of a cutting tool according to an embodiment of the present invention in combination with an alignment device according to an embodiment of the present invention.
Figure 6:
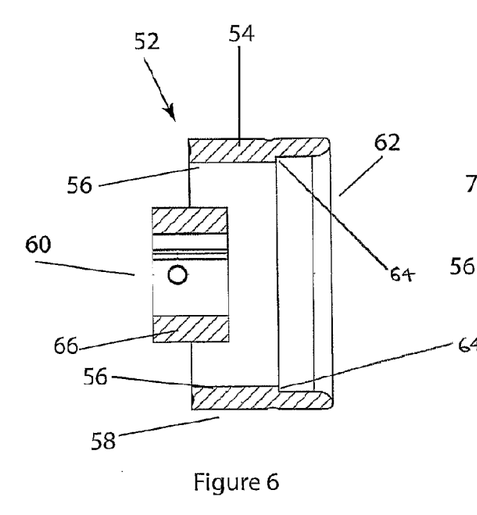
FIG. 6 shows a side view of the alignment device of FIG. 4.

FIGS. 4 to 6 show various views of a device (52) for aligning a cutting tool with a bone according to an embodiment of the present invention. The device comprises a cylindrical body (54) having an internal surface (56) and an external surface (58). The body (54) has a proximal end (60) and a distal end (62). In use, the internal surface (56) can accommodate a cutting tool and the end of a bone (see FIGS. 7 to 10).

The internal surface (56) is recessed towards the distal end (62) and the resulting ledge/flat edge (64) which extends around and is substantially perpendicular to the internal surface (56) acts as a stop when it comes into contact with the end of the bone, thereby limiting the cutting depth of the cutting tool.

Figure 7:
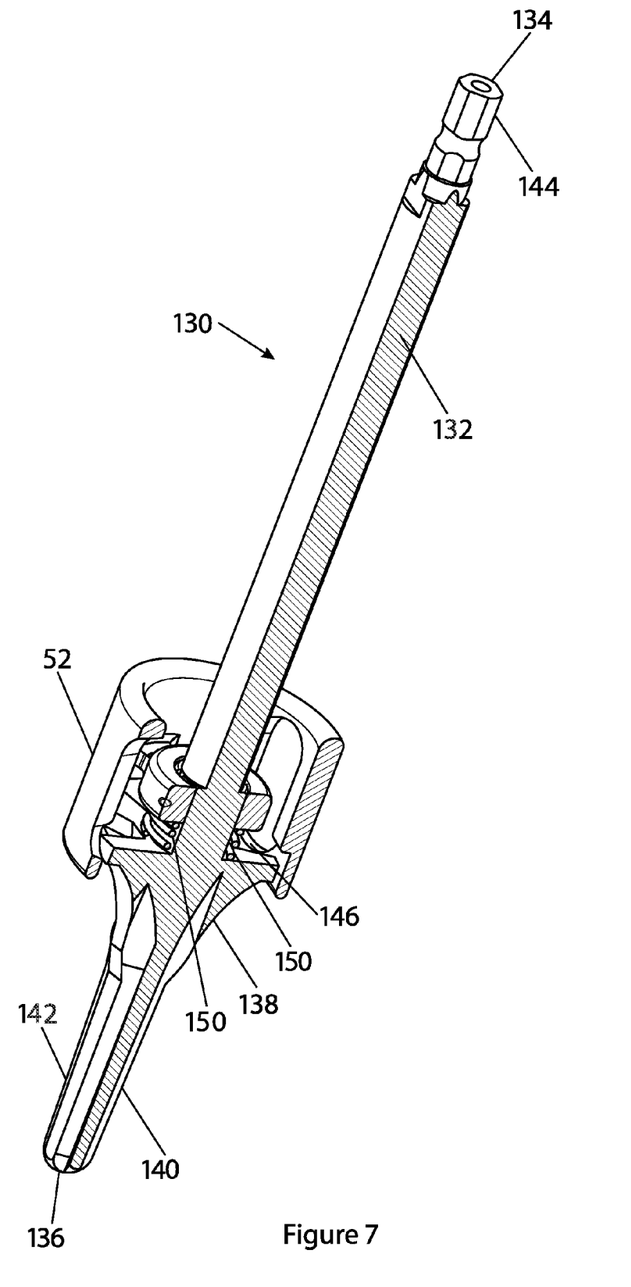
FIG. 7 shows a cross-section of a cutting tool according to an embodiment of the present invention in combination with an alignment device according to an embodiment of the present invention.

The proximal end (60) of the body (54) has an attachment means (66) for releasably attaching a cutting tool, as exemplified in FIGS. 7 and 8. The attachment means (66) comprises an open cylinder (68) that is connected to the internal surface (56) of the proximal end (60) of the body (54) by three arms (70) which are equidistantly spaced around the periphery of the open cylinder (68). The three open spaces (72) formed between the three arms (70) enable debris to flow out of the cutting tool. The open cylinder (68) has two L-shaped recesses (74) that, in use, mate with male lugs on the cutting tool in a bayonet fitting (see FIGS. 7 and 8). The cutting tool can therefore be releasably attached to the alignment device (52).

As shown in FIG. 7, the attachment means (146) also comprises a spring (50) attached to the shaft (132) proximal and adjacent to the primary cutting surfaces (138). When the alignment device (52) is attached to the cutting tool (130) the spring (150) is put under load and the tension of the spring releasably locks the alignment device (52) in position such that the male lugs are prevented from accidentally slipping out of the L-shaped recesses (74) during use.

Figure 9:
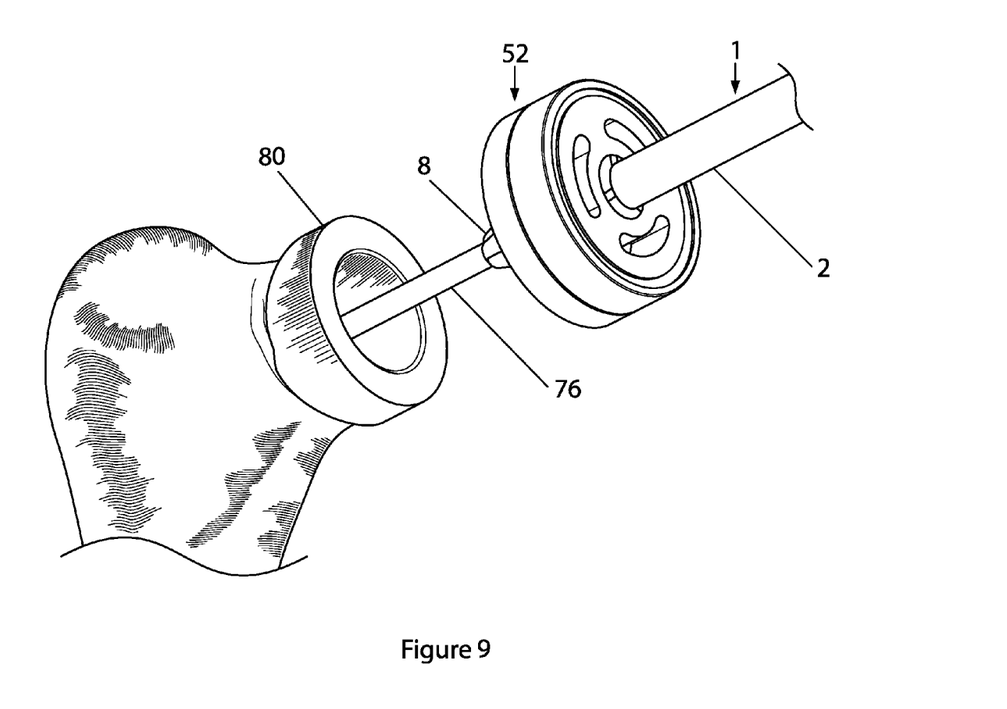
FIG. 9 shows a perspective view of a cutting tool according to an embodiment of the present invention in combination with an alignment device according to an embodiment of the present invention, in use cutting a femur.

FIGS. 9 to 14 show various stages of a mid head resection hip replacement operation using devices according to the present invention. As shown in FIG. 9, a combined cutting tool (1) and alignment device (52) as shown in FIG. 8 is selected, with the alignment device (52) having dimensions complementary to the dimensions of the resected femoral head (80). The combined cutting tool (1) and alignment device (52) assembly is aligned with the guide rod (76) and the conduit/bore of the cutting tool receives the guide rod (76). The assembly is passed down over the guide rod and a rotary power source such as a drill (not shown) is activated such that a torque is applied to the proximal end of the shaft (2). Consequently, the primary cutting surfaces (8) cut a frustoconical shaped cavity in the bone. The cutting operation is continued until the proximal end of the femur makes contact with and is stopped by the ledge/flat edge (64) of the internal surface (56) of the alignment device (52), thereby limiting the cutting depth of the cutting tool (1). The assembly is then removed from the guide rod (76).

Figure 10:
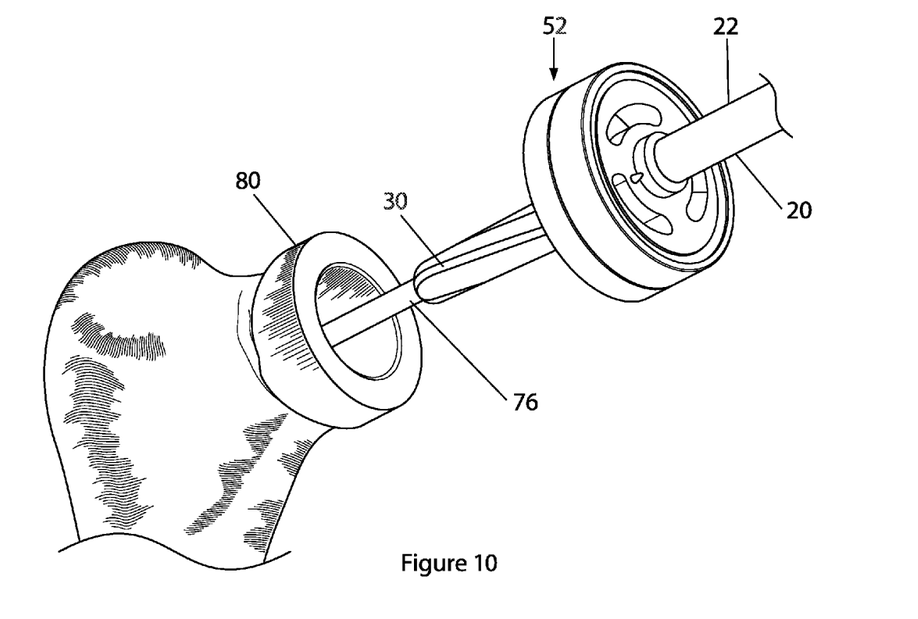
FIG. 10 shows a perspective view of a cutting tool according to an embodiment of the present invention in combination with an alignment device according to an embodiment of the present invention, in use cutting a femur.

The alignment device (52) is removed from the cutting tool (1) and attached to the cutting tool (20), as shown in FIG. 10. The combined cutting tool (20) and alignment device (52) assembly is aligned with the guide rod (76) and the conduit/bore of the cutting tool receives the guide rod (76). The assembly is passed down over the guide rod and a rotary power source such as a drill (not shown) is activated such that a torque is applied to the proximal end of the shaft (22). Consequently, the secondary cutting surfaces (30) cut a further, narrower frustoconical shaped cavity in the bone. The cutting operation is continued until the proximal end of the femur makes contact with and is stopped by the ledge/flat edge (64) of the internal surface (56) of the alignment device (52), thereby limiting the cutting depth of the cutting tool (20). The assembly is then removed from the guide rod (76).

Figure 11:
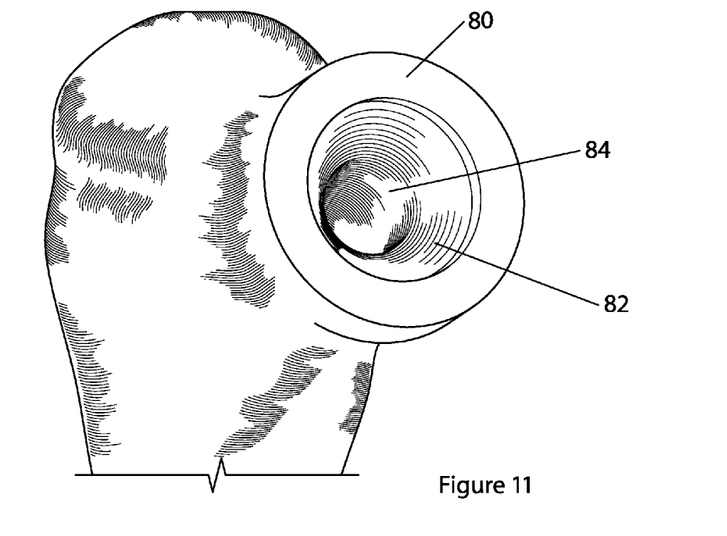
FIG. 11 shows a perspective view of a femur having a prepared cavity.
Figure 12:
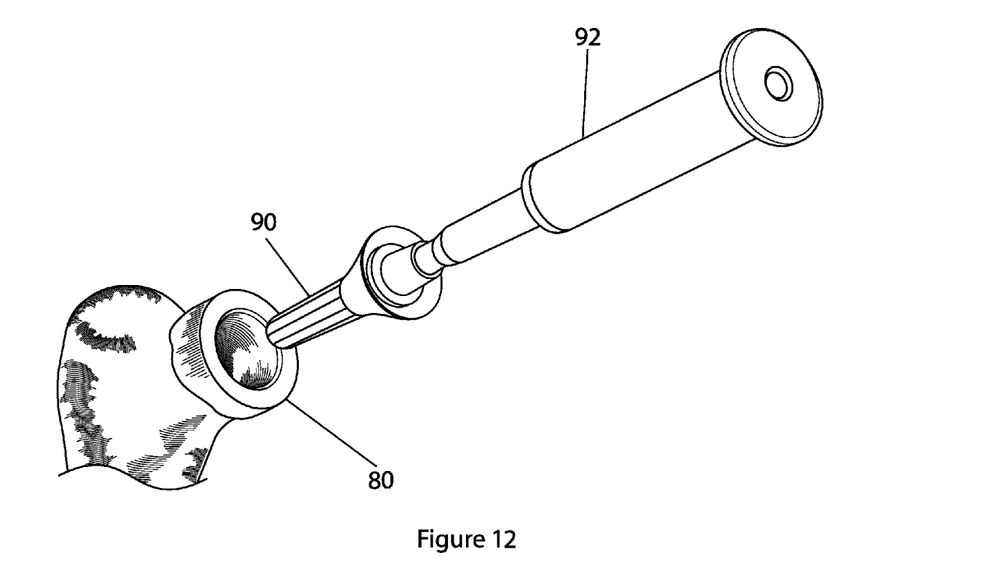
FIG. 12 shows a perspective view of a stem implant being inserted into the cavity of the femur of FIG. 11.
Figure 13:
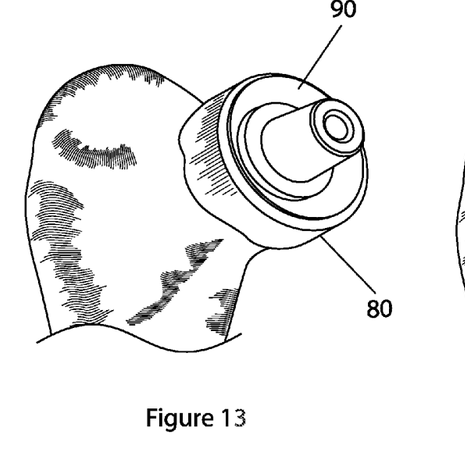
FIG. 13 shows a perspective view of a femur having the stem implant of FIG. 12 implanted.
Figure 14:
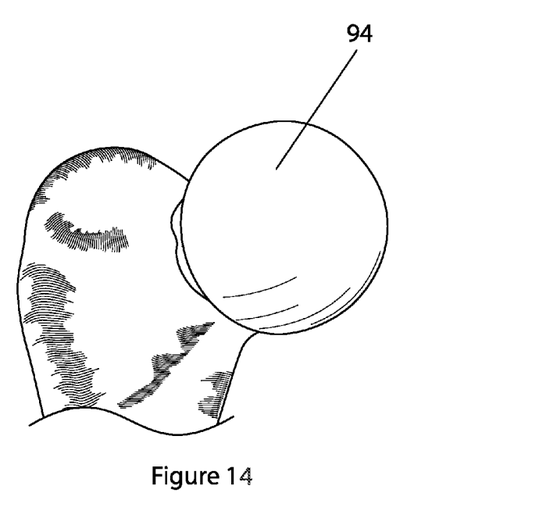
FIG. 14 shows a femur fitted with a femoral implant.

The resulting cavity prepared in the medullary canal of the resected proximal end of the femur is shown in FIG. 11. The cavity has a proximal frustoconical shaped cavity (82) which is continuous with a distal frustoconical shaped cavity (84). FIG. 12 shows a femoral stem implant (90) being inserted into the femoral head cavity (82, 84) using a stem introducer (92). FIG. 13 shows the stem implant (90) implanted in the femoral head (80). FIG. 14 shows an implant femoral head (94) attached to the stem implant (90).

The invention claimed is:

1. A bone cutting apparatus, comprising:
  (a) an elongated cutting tool comprising a longitudinal axis and a cutting tooth, positioned at a distal end of the elongated cutting tool, wherein the cutting tooth is tapered from a proximal end of the tooth to a distal end of the tooth and comprises a cutting axis and is configured to cut a conical or frustoconical shaped cavity when the cutting axis and longitudinal axis are substantially parallel and the elongated cutting tool is rotated about the longitudinal axis, wherein the elongated cutting tool further defines a cannulation extending along the longitudinal axis; and
  (b) an alignment device releasably attached to the elongated cutting tool, wherein the alignment device extends away from the elongated cutting tool, and wherein the alignment device includes at least one depth stop configured to limit a depth of cut of the elongated cutting tool.

2. The apparatus of claim 1, wherein the cutting tooth is a fluted cutting tooth having a cutting surface extending from the proximal end of the tooth to the distal end of the tooth.

3. The apparatus of claim 2, further comprising at least one additional fluted cutting tooth.

4. The apparatus of claim 3, wherein the fluted cutting teeth run parallel to the longitudinal axis of the cutting tool.

5. The apparatus of claim 4, wherein the fluted cutting teeth end at the alignment device.

6. The apparatus of claim 5, wherein the cutting surface is arcuate.

7. The apparatus of claim 3, wherein the fluted cutting teeth twist around the longitudinal axis of the cutting tool.

8. The apparatus of claim 1, further comprising a primary cutting surface and a secondary cutting surface disposed on the cutting tooth, the secondary cutting surface disposed distally on the cutting tooth relative to the primary cutting surface, wherein the secondary cutting surface is configured to cut a conical or frustoconical shaped cavity when the elongated cutting tool is rotated about the longitudinal axis.

9. The apparatus of claim 8, wherein the secondary cutting surface comprises a conical section.

10. The apparatus of claim 1, wherein the at least one depth stop is a planar surface that is perpendicular to the longitudinal axis of the elongated cutting tool.

11. The apparatus of claim 1, wherein the alignment device defines a cavity at least partially extending about the elongated cutting tool when the alignment device is releasably attached to the elongated cutting tool.

12. The apparatus of claim 1, wherein the alignment device further comprises an interior wall defining the cavity.

13. The apparatus of claim 12, wherein the interior wall is parallel to the longitudinal axis of the elongated cutting tool.

14. The apparatus of claim 13, wherein the depth stop is a planar surface extending from the interior wall.

15. The apparatus of claim 13, wherein the depth stop is a shoulder formed in the interior wall.

16. The apparatus of claim 12, wherein the interior wall is arcuate.

17. The apparatus of claim 16, wherein the interior wall is cylindrical.

18. The apparatus of claim 1, further comprising a guide rod configured to be slidably received by the cannulation of the elongated cutting tool.

19. The apparatus of claim 1, wherein the cutting tooth comprises a conical section.

20. The apparatus of claim 1, wherein the depth stop is proximal to the cutting tooth.

21. A bone cutting apparatus, comprising:
  (a) an elongated cutting tool comprising a longitudinal axis and a cutting tooth, positioned at a distal end of the elongated cutting tool, wherein the cutting tooth is tapered from a proximal end of the tooth to a distal end of the tooth and comprises a cutting axis and is configured to cut a conical or frustoconical shaped cavity when the cutting axis and longitudinal axis are substantially parallel and the elongated cutting tool is rotated about the longitudinal axis; and
  (b) an alignment device releasably attached to the elongated cutting tool, wherein the alignment device extends away from the elongated cutting tool, and wherein the alignment device comprises an interior wall defining a cavity and at least one depth stop configured to limit a depth of cut of the elongated cutting tool, wherein the at least one depth stop is a planar surface that is perpendicular to the longitudinal axis of the elongated cutting tool and is formed in the interior wall of the alignment device.

22. The apparatus of claim 21, wherein the cavity of the alignment device at least partially extends about the elongated cutting tool when the alignment device is releasably attached to the elongated cutting tool.

23. The apparatus of claim 21, wherein the interior wall is parallel to the longitudinal axis of the elongated cutting tool.

24. The apparatus of claim 21, wherein the depth stop is a shoulder formed in the interior wall.

25. The apparatus of claim 21, wherein the interior wall is arcuate.

26. The apparatus of claim 21, wherein the cutting tooth comprises a conical section.

27. The apparatus of claim 21, wherein the depth stop is proximal to the cutting tooth.

* * * * *